United States Patent [19]

Guittard et al.

[11] Patent Number: 4,966,769
[45] Date of Patent: * Oct. 30, 1990

[54] METHOD FOR DELIVERING DOSAGE FORM FOR DILTIAZEM

[75] Inventors: George V. Guittard, Cupertino; Patrick S. L. Wong, Hayward; Felix Theeuwes, Los Altos; Richard Cortese, Cupertino, all of Calif.

[73] Assignee: ALZA Corporation, Palo Alto, Calif.

[*] Notice: The portion of the term of this patent subsequent to Aug. 22, 2006 has been disclaimed.

[21] Appl. No.: 350,440

[22] Filed: May 11, 1989

Related U.S. Application Data

[63] Continuation of Ser. No. 201,519, Jun. 2, 1988, Pat. No. 4,859,470.

[51] Int. Cl.⁵ .............................................. A61K 9/24
[52] U.S. Cl. ................................... 424/473; 424/468; 424/469
[58] Field of Search ...................... 424/473, 469, 468

[56] References Cited

U.S. PATENT DOCUMENTS

| | | | |
|---|---|---|---|
| 3,845,770 | 11/1974 | Theeuwes et al. | 128/260 |
| 3,916,899 | 11/1975 | Theeuwes et al. | 128/260 |
| 4,063,064 | 12/1977 | Saunders et al. | 219/121 L |
| 4,088,864 | 5/1978 | Theeuwes et al. | 219/121 LM |
| 4,111,202 | 9/1978 | Theeuwes | 128/260 |
| 4,160,452 | 7/1979 | Theeuwes | 128/260 |
| 4,200,098 | 4/1980 | Ayer et al. | 128/260 |
| 4,235,236 | 11/1980 | Theeuwes | 128/260 |
| 4,285,987 | 8/1981 | Ayer et al. | 427/3 |
| 4,684,524 | 8/1987 | Eckenhoff et al. | 424/473 |
| 4,783,337 | 11/1988 | Wong et al. | 424/468 |

Primary Examiner—Merrell C. Cashion, Jr.
Assistant Examiner—Leon R. Horne
Attorney, Agent, or Firm—Edward L. Mandell; Paul L. Sabatine; Steven F. Stone

[57] ABSTRACT

A device is disclosed for delivering diltiazem at a controlled and substantially zero order rate over a prolonged period of time.

5 Claims, 2 Drawing Sheets

METHOD FOR DELIVERING DOSAGE FORM FOR DILTIAZEM

This appln. is a cont. of U.S. pat. appln. Ser. No. 07/201,519 filed 2 June 1988 now U.S. Pat. No. 4,859,470 issued Aug. 22, 1989. Appln. Ser. No. 07/201,519 is incorporated herein by reference and benefit is claimed of its filing date. These applns. are assigned of record to ALZA Corporation of Palo Alto, Calif.

FIELD OF THE INVENTION

This invention pertains to a dosage form comprising a member selected from the group consisting of diltiazem and its pharmaceutically acceptable salts. The invention also concerns a method for administering diltiazem and its acceptable salts for treating angina.

BACKGROUND OF THE INVENTION

The drug diltiazem chemically is 1,5-benzothiazepin-4(5H)one,3-(acetyloxy) -5-[2-(dimethylamino)ethyl]-2,3-dihydro-2-(4-methoxyphenyl). Diltiazem is therapeutically indicated as a calcium ion influx inhibitor, which activity is known also as calcium channel blocker and as calcium antagonist.

The biological activity of diltiazem is its ability to inhibit the influx of calcium ions during membrane depolarization of cardiac and vascular smooth muscles. The drug diltiazem and its pharmaceutically acceptable salts is a potent dilator of coronary arteries, both epicardial and subendocardial. Diltiazem exhibits the ability to increase exercise tolerance due to diltiazem's ability to reduce myocardial oxygen demand. This biological activity is effective by a reduction in the heart rate and the systemic blood pressure in submaximal and maximal exercise work loads. These activities indicate diltiazem is useful for the management of myocardial ischemia and angina due to coronary artery spasm.

Presently diltiazem is administered by conventional non-rate controlled tablets in single doses of 30 to 120 milligrams taken three or four times a day. This administration results in detectable plasma levels within about 30 to 60 minutes and peak levels in about two to three hours after diltiazem administration. The therapeutic level for diltiazem is about 50 to 200 nanograms per milliliter of plasma, as reported in *Physician's Desk Reference.* 42nd Ed., pp 1221-22, (1988).

In the light of the above presentation, it will be appreciated by those versed in the pharmaceutical dispensing art, to which this invention pertains, that a pressing need exists for a dosage form that delivers diltiazem at a controlled rate to a patient in critical need of cardiovascular diltiazem therapy. The pressing need exists also for an oral dosage form that delivers diltiazem at a controlled rate and at a constant dose per unit time over a prolonged period of time. The need exists for a rate controlled dosage form for the gastrointestinal delivery of diltiazem for obtaining diltiazem's beneficial hemodynamic effects by a dosage form that is free of fluid wash-out of diltiazem from the dosage form and delivers it at a controlled rate that is substantially independent of the variable environment of the gastrointestinal tract. It will be appreciated further by those versed in the dispensing art that such a novel and unique dosage form that can administer diltiazem at a rate controlled dose over time and, simultaneously, provide cardiovascular therapy would represent both an advancement and a valuable improvement in the medical art.

OBJECTS OF THE INVENTION

Accordingly, in view of the above presentation, it is an immediate object of this invention to provide a dosage form for delivering diltiazem in a rate controlled amount and wherein the dosage form substantially overcomes the deficiencies associated with the prior art.

Another object of the present invention is to provide a dosage form for administering diltiazem and it addition salts in a rate controlled dose of a prolonged period up to thirty hours for cardiovascular therapy including ischemia and angina pectoris.

Another object of the present invention is to provide a pharmaceutical dosage form that makes available sustained and controlled diltiazem therapeutic activity.

Another object of the invention is to provide a novel dosage form manufactured as an osmotic device that can administer diltiazem to a biological receptor site to produce the desired pharmaceutical effect.

Another object of the present invention is to provide a dosage form manufactured as an osmotic device that substantially reduces and/or eliminates the unwanted influences of the gastrointestinal tract, and which osmotic device still provides controlled administration of diltiazem over time.

Another object of the present invention is to provide a dosage form manufactured as an osmotic device comprising a composition that substantially reduces and/or eliminates fluid wash-out of diltiazem during the drug delivery period of diltiazem and its salts.

Another object of the invention is to provide an osmotic device adapted and sized for orally administering diltiazem, which dosage form comprises a first composition comprising diltiazem and a contacting second composition that acts in harmony for the rate controlled administration of diltiazem to the gastrointestinal tract of a warm-blooded animal.

Another object of this invention is to provide a complete pharmaceutical regimen comprising a composition comprising diltiazem that can be dispensed from a dosage form, the use of which requires intervention only for initiation and possible termination of the regimen.

Another object of this invention is to provide a method for treating cardiovascular diseases by orally administering a member selected from the group consisting of diltiazem and its acceptable salts in a rate controlled dose per unit time to a warm-blooded animal, including humans, in need of cardiovascular therapy.

Other objects, features and advantages of this invention will be more apparent to those versed in the dispensing art from the following detailed specification taken in conjunction with the drawings and the accompanying claims.

BRIEF DESCRIPTION OF THE DRAWINGS

In the drawing figures, which are not drawn to scale, but are set forth to illustrate various embodiments of the invention, the drawings figures are as follows.

In the drawings and in the specification like parts in related figures are identified by like numbers. The terms appearing earlier in the specification and in the description of the drawings, as well as embodiments thereof, are further described elsewhere in the disclosure.

DETAILED DESCRIPTION OF THE DRAWINGS

Figure 1:
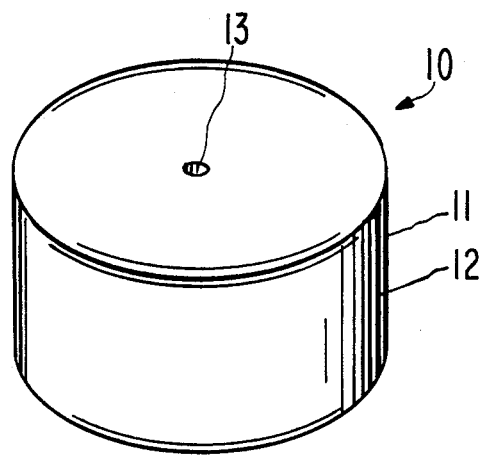
FIG. 1 is a view of a dosage form made as an osmotic device shaped and sized for orally administering the beneficial drug diltiazem to the gastrointestinal tract over a prolonged period of time.

Turning now to the drawing figures in detail, which drawing figures are an example of the dosage form provided by the invention and which example is not to be considered as limiting, one example of the osmotic dosage form is illustrated in FIG. 1 and in FIG. 2.

In FIG. 1, an osmotic dosage form is designated by the numeral 10. Dosage form 10 comprises a body member 11 comprising wall 12. Wall 12 surrounds and defines an internal compartment not seen in FIG. 1. Dosage form 10 comprises at least one passageway 13 for connecting the interior of dosage form 10 with the exterior environment of use.

Figure 2A:
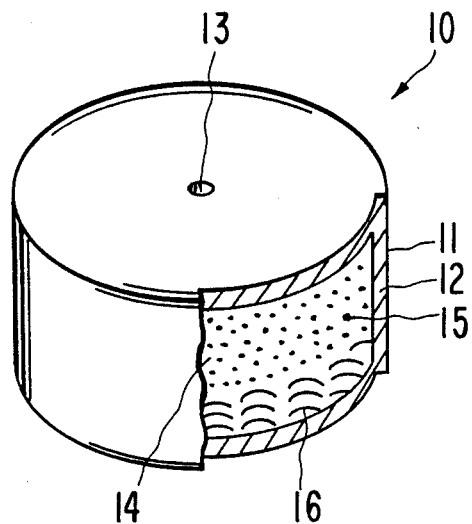
FIG. 2a and 2b are a partially opened view of the dosage form of FIG. 1 with a part of the wall of the dosage form removed for illustrating the structure of the dosage form.
Figure 2B:
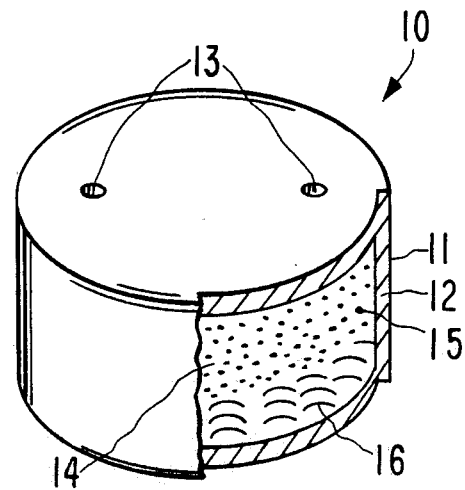

In FIG. 2a, osmotic dosage form 10 is seen in opened view for illustrating the internal structure of dosage form 10. In FIG. 2a, dosage form 10 comprises body 11 and wall 12. Wall 12 surrounds and defines an internal compartment 14. Wall 12 comprises at least one passageway 13 or, optionally, more than one exit passageway, as seen in FIG. 2b, for dispensing a member selected from the group consisting of diltiazem 15 and its pharmaceutically acceptable salts in compartment 14 from dosage form 10. The optionally preferred two passageways are useful for avoiding occasional blockage thereof by the gel comprising the diltiazem layer.

Wall 12 of dosage form 10 comprises a composition that is permeable to the passage of an exterior fluid present in the environment of use, and it is substantially impermeable to the passage of diltiazem 15 and its salts, and to other ingredients in compartment 14. Wall 12 is substantially inert, and it maintains its physical and chemical integrity during the drug dispensing life of dosage form 10. The phrase, "keeps its physical and chemical integrity," means wall 12 does not lose its structure and it does not change during the dispensing life of dosage form 10. Wall 12, in a presently preferred embodiment, comprises a member selected from the group consisting of a cellulose ester, a cellulose ether and a cellulose ester-ether. In a more preferred embodiment, wall 12 comprises a member selected from the group consisting of a cellulose acylate, cellulose diacylate, cellulose triacylate, cellulose acetate, cellulose diacetate, cellulose triacetate, and ethyl cellulose. The polymeric members comprising wall 12 comprise cellulose acetate having a degree of substitution up to 1 and an acetyl content up to 21%, cellulose diacetate having a degree of substitution of 1 to 2 and an acetyl content of 21% to 35%, cellulose triacetate having a degree of substitution of 2 to 3 and an acetyl content of 35% to 44%, and ethyl cellulose comprising an ethoxy group degree of substitution of 1.5 to 3, about 40% to 50% ethoxy content, and a viscosity range of 7 to 100 centipoises, or higher. The amount of a cellulosic polymer in wall 12 of dosage form 10 is usually from 65 weight percent (wt %) to 100 wt %. The polymers are known to the art in U. S. Pat. Nos. 3,845,770; 3,916,899 and in 4,160,020; and in *Handbook of Common Polymers* by J. R. Scott and W. J. Roff, (1971) published by CRC Press, Cleveland, Ohio.

Wall 12 of dosage form 10, optionally, comprises a hydroxypropylmethylcellulose flux enhancer for aiding in governing the fluid flux through wall 12 per unit time. The hydroxypropylmethylcellulose used for the purpose of this invention exhibits a molecular weight of about 9,200 to 16,000. The amount of hydroxypropylmethylcellulose optionally present in wall 12 generally comprises from 1 wt % to 15 wt %. Wall 12 comprises, optionally, a polyethylene glycol flux enhancer for aiding in governing fluid flux through semipermeable wall 12. The polyethylene glycol comprises a molecular weight range of 1500 to 7500. The concentration of polyethylene in wall 12, optionally, comprises from 1 wt % to b 15 wt %. The total concentration of all ingredients in wall 12 is 100 wt %.

Internal compartment 24 comprises a member selected from the group consisting of diltiazem and its pharmaceutically acceptable salts 15. Representative of nontoxic, pharmaceutically acceptable salts of diltiazem comprise a member selected from the group consisting of the hydrochloride, hydrobromide, sulfate, phosphate, lactate, citrate, tartrate, malate, maleate, fumurate, ascorbate, gulconate, asparate, salicylate, and the like. Internal compartment 14 comprises diltiazem and its acid addition salts in an amount of from 30 mg to 500 mg, with presently preferred individual dosage forms comprising 60 mg, 120 mg, 180 mg, 240 mg, 300 mg, 360 mg, 400 mg, 425 mg, and the like.

Diltiazem therapeutically acceptable salts are highly soluble in water, in artificial gastric fluid and in artificial intestinal fluid. For example, the solubility of diltiazem hydrochloride at 37° C. in water is 612 mg/ml, in artificial gastric fluid it is 668 mg/ml, and in artificial intestinal fluid it is 611 mg/ml. This high solubility leads-away from incorporating and delivering diltiazem by an osmotic dosage form in view of the prior art disclosure in *J. Pharmaceutical Sciences*, Vol. 64, No. 12, pp 1987 to 1991, (1975). The reference teaches that less than forty percent of diltiazem would be delivered at a zero order rate from an osmotic system. The mass of diltiazem delivered is ascertained from the mass delivery zero order equation as follows:

$$\frac{m_z}{m_t} = 1 - \frac{S}{\rho}$$

wherein $m_t$ is the total mass of drug diltiazem contained in the osmotic system, $m_z$ is the mass of diltiazem delivered at zero order, $\rho$ is the density of the diltiazem core, and S is the solubility of diltiazem.

This invention unexpectedly discovered diltiazem could have a mass delivered greater from an osmotic system greater than ninety percent by providing the osmotic system with an unobvious diltiazem core. The diltiazem core comprises from 70 wt % to 96 wt % of a member selected from the group consisting of diltiazem and its acceptable salts; from 0.5 wt % to 15 wt % of an acrylic acid polymer of the formula:

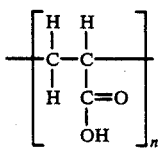

wherein n is a positive number for providing an acrylic acid polymer comprising a molecular weight of 2,500,000 to 4,000,000; from 0.5 wt % to 20 wt % of a polymer of the formula

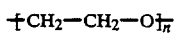

wherein n is a positive whole number for providing a polyethylene oxide comprising a molecular weight of 4,000,000 to 5,500,000: from 0.5 wt % to 20 wt % of a polyvinylpyrrolidone comprising a molecular weight of 35,000 to 40,000 and from 0 wt % to 5 wt % of a member selected from the lubricants consisting of magnesium stearate and stearic acid, with the weight of all ingredients comprising the diltiazem core equals to 100 wt %.

Dosage form 10 in compartment 14 comprises a push composition 16. Push composition 16, when dosage form 10 is in operation in a fluid environment of use, pushes diltiazem core 15 from dosage form 10. Push composition 16 comprises from 70 wt % to 95 wt % of a polyethylene oxide comprising a molecular weight of about 6,200,000 to 7,500,000; from 1 wt % to 20 wt % of an osmagent selected from the group consisting of an osmotically active salt, carbohydrate, polysaccharide, oxide and acid solute; from 1 wt % to 15 wt % of a hydroxypropylmethylcellulose comprising a molecular weight of about 9,000 to 16,000; and from 0.0 wt % to 3 wt % of ferric oxide, with the weight of all ingredients in push composition 16 equal to 100 wt %.

The expression, "exit passageway 13," comprises means and methods suitable for dispensing the beneficial drug diltiazem 15 from dosage form 10. The exit means include at least one passageway that passes through wall 12 for communicating diltiazem in compartment 14 with the exterior of dosage form 10. The expression, "at least one passageway," includes aperture, orifice, bore, pore, porous element through which diltiazem can be dispensed, a hollow fiber, capillary tube, microporous insert, microporous overlay, and the like. Thus, a wall that is at least in part microporous is optional with the invention. The expression includes a material that erodes or is leached from wall 12 in the fluid environment of use to produce at least one passageway of controlled releasing dimensions. Representative materials suitable for forming at least one passageway, two passageways, or more, include an erodible poly(glycolic) or poly(lactic) acid member in the wall, a gelatinous filament, poly(vinyl alcohol), leachable materials such as fluid removable pore formers providing exit pores of release rate controlling properties, and the like. A passageway or a plurality of passageways can be formed by leaching a material such as sorbitol from the wall. The passageway can have any shape such as round, triangular, square, elliptical, irregular, and the like. The dosage form can be constructed with one or more passageways in a spaced apart relation on more than a single distant surface of a dosage form. Passageways and equipment for forming passageways are disclosed in U. S. Pat. Nos. 3,916,889; 4,063,064 and 4,088,864. Representative passageways formed by governed leaching to produce a pore of precontrolled size are disclosed in U. S. Pat. No. 4,200,098.

Dosage form 10 is manufactured by standard techniques. For example, in one manufacture diltiazem and the other ingredients comprising the diltiazem core are homogeneously blended and pressed into a solid core. The core possesses dimensions that correspond to the internal dimension of the area occupied by core 15 in the dosage form 10. The core also possesses dimensions corresponding to the dimensions of the push composition for forming a contacting surface arrangement therewith. In this manufacture, diltiazem and the other ingredients comprising the core are blended with a solvent and mixed into a solid or semisolid form by conventional methods such as ballmilling, calendering, stirring or rollmilling and then pressed into a preselected shape. Next, the push composition is placed in contact with the drug core. The drug core, push composition can be placed in contacting arrangement by using a conventional two-layered press. The contacting drug core, push composition are coated with a semipermeable wall. The wall can be applied by compression coating, molding, spraying, dipping, or air suspension procedures. The air suspension and the air tumbling procedures comprise suspending and tumbling the pressed drug core, and the push composition in a current of air containing the wall forming composition.

In another manufacture, dosage form 10 is manufactured by the wet granulation technique. In the wet granulation technique, the diltiazem and the ingredients comprising the diltiazem composition are blended using an organic cosolvent, such as isopropyl alcohol-methylene dichloride 80/20 v/v (volume/volume) as the granulation fluid. The ingredients forming the diltiazem composition are passed through a 40 mesh screen and thoroughly blended in a mixer. Other optional ingredients comprising the diltiazem composition are dissolved in a portion of the granulation fluid and added to the drug blend with continual mixing in the blender. The granulating fluid is added until a blend is produced, which wet blend is then forced through a 20 mesh screen onto oven trays. The blend is dried for 18 to 24 hours at 50° C. in a forced air oven. The dried granules are then sized through a 20 mesh screen. Next, a lubricant such as magnesium stearate, which has been passed through an 80 mesh screen, is added to the dry screened granules and blended in a V-blender for 5 to 10 minutes. The composition is pressed into a layer, for example, in a 3-station Manesty ® layer press. The speed of the press is set at 30 rpm and the maximum load set at 2 tons. The diltiazem layer is pressed against the push composition and the bilayer drug core fed to a coating machine.

Another manufacturing process that can be used for providing the drug core, push composition comprises blending the powdered ingredients comprising the drug core, or the push composition separately in a fluid bed granulator. After the powdered ingredients are dry blended in the granulator, a granulating fluid, for example, poly(vinylpyrrolidone) in water, is sprayed onto the powders. The coated powders then are dried in the granulator. This process granulates all the ingredients present therein while adding the granulating fluid. After the granules are dried a lubricant, such as stearic acid or magnesium stearate is added to the granules in a V- blender and blended 5 to 10 minutes. The granules then are pressed in the manner described above.

DESCRIPTION OF EXAMPLES OF THE INVENTION

The following examples are merely illustrative of the present invention and they should not be considered as limiting the scope of the invention in any way, as these examples and other equivalents thereof will become more apparent to those versed in the dispensing art in the light of the present disclosure, the drawing figures, and the accompanying claims.

EXAMPLE 1

A device for delivering diltiazem is made as follows: first, 9.40 kg of diltiazem hydrochloride, 0.10 kg of Carbomer ®-934-P acrylic acid polymer having am molecular weight of about 3,000,000, and 0.20 kg of polyethylene oxide having a molecular weight of about 5,000,000 are added to a blender and blended for 18 minutes to produce a uniform mix. Next 0.20 kg of polyvinylpyrrolidone having a molecular weight of about 38,000 is mixed with 350 ml of anhydrous ethyl alcohol to form a granulation fluid. Then, the granulating fluid is added slowly to the blended ingredients, and all the ingredients blended to produce a wet mass. The wet mass is dried in a forced air oven for 17 to 23 hours at room temperature, about 25° C., to evaporate the ethyl alcohol. Then, the dry granules are given an additional drying for 2 to 4 hours at 50° C. The dry granules are then passed through a 30 mesh screen. Next, 0.10 kg of the lubricant magnesium stearate is added to the dry blend and blended for 9 minutes to produce a homogeneous composition. The diltiazem composition is stored until a push composition is prepared for making the final assembled device.

The push composition is made as follows: first, 4.35 kg of polyethylene oxide having a 7,000,000 molecular weight, 0.35 kg of sodium chloride, and 0.25 kg of hydroxypropylmethylcellulose having a viscosity of 5 centipoises are blended in a blender for 8.2 minutes to produce a uniform blend. Next, 350 ml of denatured, anhydrous ethyl alcohol is added as a granulating fluid to produce a wet mass. Next the granulated wet mass is passed through a 30 mesh screen to form wet granules. The wet granules next are spread onto trays and the wet granules dried at room temperature of 25° C. for 20 to 25 hours. The dry granules then are passed through a 20 mesh screen. The push composition now is ready for manufacturing the final device.

The granules comprising the diltiazem compositions are transferred to the number one feed of a hopper and the granules comprising the push composition are fed to the number two feed of a hopper. The feed hoppers are placed onto a bi-layer press and the diltiazem composition pressed onto the push composition.

Next, the pressed compositions are surrounded with a semipermeable wall. The wall forming composition is prepared as follows: first, a cosolvent is prepared by mixing 80 parts of methylene chloride with 20 parts of methanol (wt/wt) and cellulose acetate having an acetyl content of 39.8% slowly added thereto. Then, hydroxypropylmethylcellulose having a 11,300 molecular weight is added to the cosolvent with stirring followed by the addition of polyethylene glycol having a 3350 molecular weight. The wall forming ingredients dissolved in the cosolvent to produce a cosolvent comprising 80% cellulose acetate, 10% hydroxypropylmethylcellulose, and 10% polyethylene glycol, to obtain 3% solids. The pressed compositions are placed in a coating unit, and the pressed compositions coated with a semipermeable wall.

Next the wall coated compositions are removed from the coater and an exit port is drilled through the wall by a laser. The dosage forms are then dried in a humidity over at 50% RH and 50° C. for 48 hours to remove all residual solvent. The dosage forms are sized and shaped for oral admittance into the gastrointestinal tract of a human.

The device provided by this manufacture comprises a diltiazem dose of 360 mg. The diltiazem composition comprises 94 wt % diltiazem, 1 wt % acrylic acid polymer, 2 wt % of polyethylene oxide coagulant 5,000,000 molecular weight, 2 wt % polyvinylpyrrolidone, and 1 wt % magnesium stearate. The push composition weighed 135 mg and comprises 87 wt % polyethylene oxide molecular weight 7,000,000, 7 wt % sodium chloride, 5 wt % hydroxypropylmethylcellulose and 1 wt % ferric oxide. The semipermeable wall comprises 80 wt % cellulose acetate, 10 wt % polyethylene glycol and 10 wt % hydroxypropylmethylcellulose. The device delivers diltiazem for 24 hour at an average delivery rate of 15.3 mg/hr.

EXAMPLE 2

Figure 3:
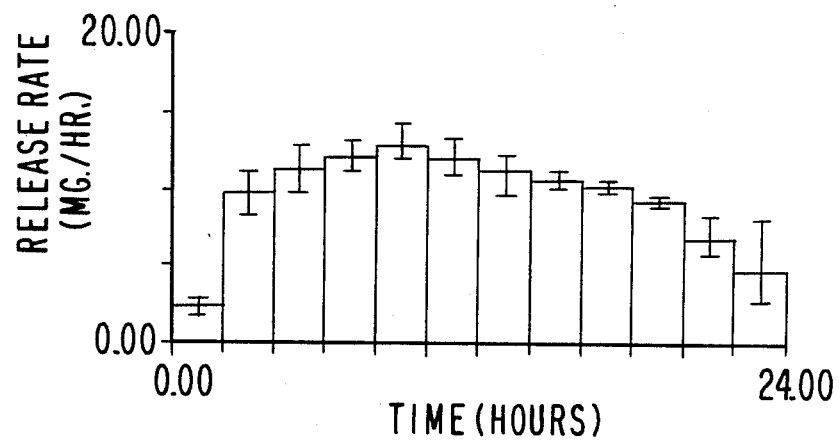
FIG. 3 is a graph that illustrates the rate of release of diltiazem for a device provided by the invention; and, FIG. 4 is a graph that illustrates the cumulative amount of diltiazem released over 24 hours.

The procedure of Example 1 is followed to provide a device comprising the following: a diltiazem composition comprising 240 ml dose of diltiazem with a 10 % over does in the composition, 2.81 mg of acrylic acid polymer having a 3,000,000 molecular weight, 5.62 mg of poly(ethylene oxidel coagulant having a 5,000,000 molecular weight, 5.62 mg of poly(vinylpyrrolidone) having a 38,000 molecular weight, and 2.81 mg of magnesium stearate; a push composition comprising 80.25 mg of poly(ethylene oxide) 303 having a 7,000,000 molecular weight, 6.46 mg of sodium chloride, 4.61 mg of hydroxypropylmethylcellulose having a 9,200 molecular weight, and 0.92 mg of ferric oxide; and a semipermeable wall weighing 22.20 mg comprising 80% cellulose acetate having a 39.8% acetyl content, 10% hydroxypropylmethylcellulose having a 11,200 molecular weight and 10% polyethylene glycol having a 3350 molecular weight. The device comprises two 15 mil passageways and exhibits the rate of release in milligrams per hour as seen in FIG. 3.

EXAMPLE 3

Figure 4:
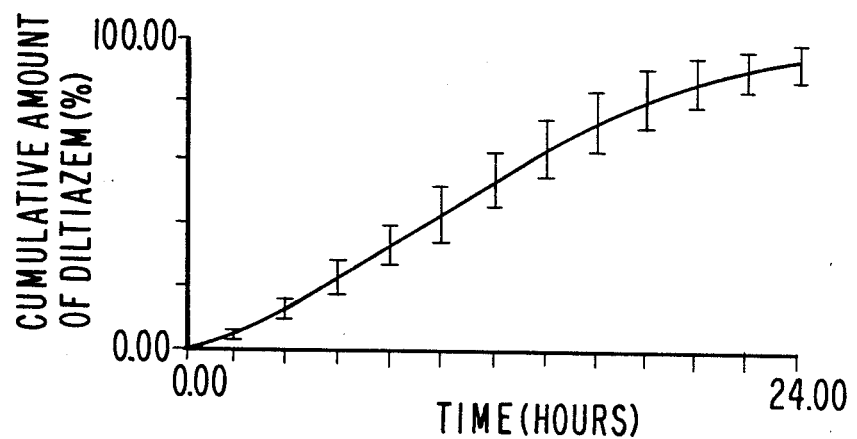

The procedure described above is followed to provide a delivery device comprising: a diltiazem composition weighing 280 mg and comprising 94% diltiazem hydrochloride, 1 % polyacrylic acid with a 3,000,000 molecular weight, 2% Povidone ® poly(vinylpyrrolidone) with a 38,000 molecular weight, and 1% stearic acid; a push composition weighing 90 mg and comprising 87% Polyox ®303 with a 7,500,000 molecular weight, 7% sodium chloride, 5% hydroxypropylmethylcellulose with a 11,200 molecular weight, and 1% ferric oxide; and a semipermeable wall weighing 21.20 mg and comprising 80% cellulose acetate comprising a 39.8% acetyl content, 10% polyethylene glycol having a 3350 molecular weight, and 10% hydroxypropylmethylcellulose having a 11,200 molecular weight. The device comprises a pair of 15 mil exit ports and a means release rate of 10.2 mg/hr. The cumulative amount of diltiazem hydrochloride release is seen in FIG. 4.

EXAMPLE 4

The example pertains to a method for delivering a member selected from the group consisting of diltiazem and its pharmaceutically acceptable salts to a human patient in need of diltiazem and its salts, which method comprises:

(a) admitting orally into the human a device comprising:
  (1) a wall comprising a semipermeable composition, said wall surrounding and defining a compartment, which compartment comprises:
    (A) a diltiazem composition comprising from 70 wt % to 96 wt % of a member selected from the group consisting of diltiazem and its pharmaceutically acceptable salts, from 0.5 wt % to 15 wt % of polyacrylic acid comprising a 2,500,000 to 4,000,000 molecular weight, from 0 5 wt % to 20 wt % of a poly(ethylene oxide) comprising a 4,000,000 to 5,500,000 molecular weight, and from 0.5 wt % to 20 wt % of a poly(vinylpyrrolidone) comprising a 35,000 to 40,000 molecular weight.
    (B) a push composition comprising from 70 wt % to 95 wt % of poly(ethylene oxide) comprising a 6,200,000 to 7,500,000 molecular weight, from 1 wt % to 15 wt % of a hydroxypropylmethylcellulose comprising a molecular weight of about 9,000 to 16,000;
  (2) at least one passageway in the wall for delivering the member selected from the group consisting of diltiazem and it salts from the device, said passageway comprising a cross section of 0.25 mm to 0.64 mm; and,
(b) delivering diltiazem and its salts by the device imbibing fluid through the wall into the compartment to cause the diltiazem composition to form a dispensable composition and to cause the push composition to push the diltiazem composition through the passageway, which diltiazem or a diltiazem salt is administered to the human in need thereof.

In summary, it will be appreciated the present invention contributes to the diltiazem art an unobvious dosage form that possesses practical medical utility. While the invention has been described and pointed out in detail with reference to operative embodiments thereof, it will be understood that those skilled in the art will appreciate that various changes, modification, substitutions and omissions can be made without departing from the spirit of the invention. It is intended, therefore, that the invention embraces those equivalents within the scope of the claims.

We claim:

1. A method for delivering diltiazem to a recipient in need thereof, which method comprises:
  (a) admitting orally into the recipient a device comprising:
    (1) a wall surrounding and forming a compartment, which compartment comprises:
      (A) a diltiazem composition comprising from 70 wt % to 96 wt % of a member selected from the group consisting of diltiazem and its pharmaceutically acceptable salts, from 0.5 wt % to 15 wt % of polyacrylic acid comprising a 2,500,000 to 4,000,000 molecular weight, from 0.5 wt % to 20 wt % of a poly(ethylene oxide) comprising a 4,000,000 to 5,500,000 molecular weight, and from 0.5 wt % to 20 wt % of a poly(vinyl pyrrolidone) comprising a 35,000 to 40,000 molecular weight;
      (B) a push composition comprising from 70 wt % to 95 wt % of poly(ethylene oxide) comprising a 6,200,000 to 7,500,000 molecular weight, from 1 wt % to 20 wt % of an osmagent, and from 1 wt % to 15 wt % of a hydroxypropylmethylcellulose comprising a 9,000 to 16,000 molecular weight;
    (2) at least one passageway in the wall; and,
  (b) delivering diltiazem by the device imbibing fluid through the wall into the compartment to cause the diltiazem composition to form a dispensable composition and to cause the push composition to push the diltiazem composition through the passageway for delivering diltiazem to the recipient.

2. A method for delivering diltiazem to a recipient in need thereof, which method comprises:
  (a) admitting orally into the recipient a dosage form comprising:
    (1) a wall comprising at least in part a composition, which composition comprises a member selected from the group consisting of a cellulose ester, cellulose ether, cellulose ester-ether, cellulose acylate, cellulose diacylate, cellulose acetate, cellulose diacetate and cellulose triacetate, which wall surrounds;
    (2) a compartment;
    (3) an osmotic core in the compartment, which core comprises from 30 mg to 500 mg of a member selected from the group consisting of diltiazem and its pharmaceutically acceptable salts, wherein the salt is a member selected from the group consisting of hydrochloride, hydrobromide, sulfate, phosphate, lactate, citrate, tartrate, malate, maleate, fumarate, ascorbate, gluconate, aspartatate, and salicylate;
    (4) means in the wall for delivering diltiazem from the dosage form, said means comprising a leached passageway formed in the wall when the dosage form is in the recipient, and,
  (b) delivering from the osmotic core from 30 mg up to 500 mg of diltiazem through the leached passageway to the recipient over 24 hours.

3. The method for delivering diltiazem to the recipient in need thereof according to claim 1, wherein the leached passageway is replaced by an erodible diltiazem release rate controlling pore.

4. The method for delivering diltiazem to the recipient in need thereof according to claim 1, wherein the leached passageway is replaced by a drilled passageway.

5. The method for delivering diltiazem to the recipient in need thereof according to claim 1, wherein the recipient comprises a gastrointestinal fluid and the diltiazem exhibits solubility in gastric and intestinal fluid.

* * * * *

UNITED STATES PATENT AND TRADEMARK OFFICE
CERTIFICATE OF CORRECTION

PATENT NO. : 4,966,769

DATED : October 30, 1990

INVENTOR(S) : George V. Guittard, Patrick S.L. Wong, Felix Theeuwes, and Richard Cortese It is certified that error appears in the above-identified patent and that said Letters Patent is hereby corrected as shown below:

On the title page, item [54] and in column 1, lines 1 and 2, "METHOD FOR DELIVERING DOSAGE FORM FOR DILTIAZEM" should read --METHOD OF AMDIMINISTERING DILTIAZEM TO A RECIPIENT--.

In column 10, claim 2, in line 43, "aspartatate" should read ----aspartate----.

In column 10, claim 3, in line 52, "claim 1" should read ----claim 2----.

In column 10, claim 4, in line 56, "claim 1" should read ----claim 2----.

In column 10, claim 5, in line 60, "claim 1" should read ----claim 2----.

Signed and Sealed this

Eighth Day of September, 1992

Attest:

DOUGLAS B. COMER

Attesting Officer

Acting Commissioner of Patents and Trademarks